US008704005B2

(12) United States Patent
Dube et al.

(10) Patent No.: US 8,704,005 B2
(45) Date of Patent: Apr. 22, 2014

(54) METHODS FOR MAKING POLYGLYCEROL

(75) Inventors: Marc Dube, Ottawa (CA); Somaieh Salehpour, Ottawa (CA)

(73) Assignee: University of Ottawa, Ottawa, ON (CA)

( * ) Notice: Subject to any disclaimer, the term of this patent is extended or adjusted under 35 U.S.C. 154(b) by 0 days.

(21) Appl. No.: 13/979,589

(22) PCT Filed: Mar. 17, 2011

(86) PCT No.: PCT/IB2011/000987
§ 371 (c)(1),
(2), (4) Date: Jul. 12, 2013

(87) PCT Pub. No.: WO2012/123777
PCT Pub. Date: Sep. 20, 2012

(65) Prior Publication Data
US 2013/0289314 A1    Oct. 31, 2013

(51) Int. Cl.
*C07C 41/09* (2006.01)
*C07C 43/13* (2006.01)
*C08G 65/34* (2006.01)

(52) U.S. Cl.
CPC .............. *C07C 41/09* (2013.01); *C07C 43/135* (2013.01); *C08G 65/34* (2013.01)
USPC ......................................... 568/619; 568/623

(58) Field of Classification Search
CPC ....... C07C 41/09; C07C 43/135; C08G 65/34
USPC ................................................. 568/619, 623
See application file for complete search history.

(56) References Cited

U.S. PATENT DOCUMENTS

| | | | |
|---|---|---|---|
| 3,637,774 A | 1/1972 | Babayan et al. |
| 3,968,169 A | 7/1976 | Seiden et al. |
| 4,311,039 A | 1/1982 | Koehler et al. |
| 4,973,763 A | 11/1990 | Jakobson et al. |
| 5,635,588 A | 6/1997 | Eshuis et al. |
| 6,620,904 B2 | 9/2003 | Lemke |
| 6,664,690 B2 | 12/2003 | Huth |
| 7,335,801 B2 | 2/2008 | Endo et al. |
| 2007/0049775 A1 | 3/2007 | Endo et al. |

FOREIGN PATENT DOCUMENTS

| | | | | |
|---|---|---|---|---|
| FR | 2849023 A1 * | 6/2004 | .............. | C07C 41/09 |
| WO | WO-2007/092407 | 8/2007 | | |

OTHER PUBLICATIONS

"Product Information Polyglycerol" accessed at http://www.hyperpolymers.com/prodinf.html, on Mar. 2, 2013, 7 pages.
Behr, A. et al., "Improved Utilisation of Renewal Resources: New Important Derivatives of Glycerol," Green Chemistry, 2008, vol. 10, pp. 13-30.
Behr, A. et al., "The refinement of renewable resources: New important derivatives of fatty acids and glycerol," European Journal of Lipid Science and Technology, 2010, vol. 112, No. 1, pp. 31-50.
Bozell, J.J. et al., "Technology development for the production of biobased products from biorefinery carbohydrates—The US Department of Energy's "top 10" revisited," Green Chemistry, 2010, vol. 12, No. 4, pp. 539-554.
Cassel, S., et al. "Original Synthesis of Linear, Branched and Cyclic Oligoglycerol Standards", European Journal of Organic Chemistry, 2001, vol. 5, pp. 875-896.
Chaudhuri, S., "Global Biodiesel Market Analysis and Forecasts to 2020," GlobalData emagazine, Jun. 2010, http://www.altenergymag.com/emagazine/2010/06/global-biodiesel-market-analysis-and-forecasts-to-2020/1498, 2 pages.
Checkbiotech, "Global biodiesel market almost doubles every year between 2001 and 2009," Renewable Energy Magazine, 2010, http://bioenergy.checkbiotech.org/news/global_biodiesel_market_almost_doubles_every_year_between_2001_and_2009, 1 page.
Clacens, J. M. et al., "Selective etherification of glycerol to polyglycerols over impregnated basic MCM-41 type mesoporous catalysts", Applied Catalysis A: General 227, 2002, pp. 181-190.
Dolhaine, H., et al., "Strukturen im „Polyglycerin". Fette, Seifen, Anstrichm., 1984, vol. 86, Issue 9, pp. 339-343. doi: 10.1002/lipi.19840860902.
Dube, M.A. et al., "Biodiesel production using a membrane reactor," Bioresource Technology, 2007, vol. 98, No. 3, pp. 639-647.
Flory, P., "Molecular Size Distribution in Three-Dimensional Polymers: I. Gelation [1]". Journal of the American Chemical Society, 1941, 63 (11): 3083-3090. doi:10.1021/ja01856a061.
Gordon, M. et al., "Chemical combinatorics. Part I. Chemical kinetics, graph theory, and combinatorial entropy", Journal of the Chemical Society A: Inorganic, Physical, and Theoretical Chemistry, 1970, pp. 0729-737, DOI: 10.1039/J19700000729.
Gordon, M. et al., "Statistical Mechanics and the Critically Branched State", Nature, 1971, Issue 5324, vol. 234, pp. 96-97.
International Search Report and Written Opinion for International Application No. PCT/IB2011/000987, mailed Aug. 24, 2011, 8 pages.
Ionescu, M. et al., "High Functionality Polyether Polyols Based on Polyglycerol", Journal of Cellular Plastics, 2010, vol. 46, No. 3, pp. 223-237. DOI: 10.1177/0021955X09355887.
Johnson, D.T. et al., "The glycerin glut: Options for the value-added conversion of crude glycerol resulting from biodiesel production," Environmental Progress, 2007, vol. 26, No. 4, pp. 338-348.
Jovanovi, R. et al., "In-line monitoring of butyl acrylate/vinyl acetate emulsion copolymerizations using ATR-FTIR spectroscopy," Polymer Reaction Engineering, 2003, vol. 11, No. 3, pp. 233-257.
Kainthan, R.K. et al., "Biocompatibility Testing of Branched and Linear Polyglycidol," Biomacromolecules, 2006, vol. 7, No. 3, pp. 703-709.
Kelzer, J., "Including glycerol, a byproduct of biodiesel production, in feedlot diets," Farm and Ranch Guide: Livestock News, Feb. 14, 2010, printed on Sep. 19, 2011, 4 pages.

(Continued)

*Primary Examiner* — Rosalynd Keys
(74) *Attorney, Agent, or Firm* — Foley & Lardner LLP

(57) ABSTRACT

Methods are provided for making polyglycerol. The methods include heating glycerol at reduced pressure in the absence of a glyceride and in the presence of a catalytic amount of an acid selected from the group consisting of sulfuric acid, triflic acid, hydrochloric acid, hexafluorophosphoric acid, tetrafluoroboric acid and mixtures thereof.

22 Claims, 7 Drawing Sheets

(56) References Cited

OTHER PUBLICATIONS

Kenar, J.A., "Glycerol as a platform chemical: Sweet opportunities on the horizon?," Lipid Technology, 2007, vol. 98, No. 19, pp. 249-253.

Kumar, A. et al., "Modelling of intramolecular reactions in the step-growth polymerization of multifunctional monomers", Polymer, Apr. 1986, vol. 27, Issue 4, pp. 583-591.

Macosko, et al., "A New Derivation of Average Molecuar Weights of Nonlinear Polymers", Macromolecules, 1976, vol. 9, No. 2, pp. 199-206. DOI: 10.1021/ma60050a003.

Marquez-Alverez, C. et al., "Solid catalysts for the synthesis of fatty esters of glycerol, polyglycerols and sorbitol from renewable resources" Topics in Catalysis, 2004, vol. 27, 105-117.

Pagliaro, M. et al., "From glycerol to value-added products," Angew Chem Int Ed Engl., 2007, vol. 46, No. 24, pp. 4434-4440.

Rankin S. E. et al., "Dynamic Monte Carlo Simulation of Gelation with Extensive Cyclization", Macromolecules, 2000, vol. 33, pp. 7639-7648.

Salehpour, S. et al., "Towards the Sustainable Production of higher molecular weight polyglycerol," Macromolecular Chemistry and Physics, 2011, vol. 212, pp. 1284-1293.

Stockmayer, W. H., "Theory of Molecular Size Distribution and Gel Formation in Branched—Chain Polymers", The Journal of Chemical Physics, 1943, vol. 11, pp. 45.

Sunder, A. et al., "Controlled synthesis of hyperbranched polyglycerols by ring-opening multibranching polymerization," Macromolecules, 1999, vol. 32, No. 13, pp. 4240-4246.

Tobing, S.D. et al., "Molecular parameters and their relation to the adhesive performance of emulsion acrylic pressure-sensitive adhesives. II. Effect of crosslinking," J. Appl. Polym. Sci., 2001, vol. 79, No. 14, pp. 2558-2564.

Tokar, R. et al., "Cationic Polymerization of Glycidol : Coexistence of the Activated Monomer and Active Chain End Mechanism", Macromolecules, 1994, vol. 27, pp. 320-322.

Wilms, D. et al., "Hyperbranched Polyglycerols with Elevated Molecular Weights: A Facile Two-Step Synthesis Protocol Based on Polyglycerol Macroinitiators," Macromolecules, 2009, vol. 42, pp. 3230-3236.

Wilms, D. et al., "Hyperbranched polyglycerols: From the controlled synthesis of biocompatible polyether polyols to multipurpose applications," Accounts of Chemical Research, 2010, vol. 43, No. 1, pp. 129-141.

Yang, X. et al., "Synthesis and characterization of novel polyglycerol hydrogels containing L-lactic acid groups as pendant acidic substituents: pH-responsive polyglycero-based hydrogels," Journal of Applied Polymer Science, 2009, vol. 112, No. 6, pp. 3209-3216.

Zhou, C.H. et al., "Chemoselective catalytic conversion of glycerol as a biorenewable source to valuable commodity chemicals," Chem. Soc. Rev., 2008, vol. 37, No. 3, pp. 527-549.

International Preliminary Report on Patentability for Intl. Pat. Appin. No. PCT/IB2011/000987 dtd Sep. 26, 2013.

Martin, A. et al., "Oligomerization of glycerol—a critical review," Eur. J. Lipid Sci. Technol., 2011, vol. 113, pp. 100-117.

Medeiros, M.A. et al., "Acid-Catalyzed Oligomerization of Glycerol Investigated by Electrospray Ionization Mass Spectrometry," J. Braz. Chem. Soc., 2009, vol. 20, No. 9, pp. 1667-1673.

Rokicki, G. et al., "Hyperbranched aliphatic polyethers obtained from environmentally benign monomer: glycerol carbonate," Green Chem., 2005, vol. 7, pp. 529-539.

\* cited by examiner

METHODS FOR MAKING POLYGLYCEROL

CROSS-REFERENCE TO RELATED APPLICATION

The present application is a U.S. national stage application claiming the benefit of International Application No. PCT/IB2011/000987, filed on Mar. 17, 2011, the entire contents of which are incorporated herein by reference in their entirety.

FIELD

The present technology relates generally to methods of making polyglycerol.

BACKGROUND

The following description is provided to assist the understanding of the reader. None of the information provided or references cited is admitted to be prior art to the present technology.

In recent years, interest in bio-based polymers has grown tremendously. Such polymers present a lower environmental burden and are attractive alternatives to conventional petroleum-based polymers. Polyglycerol is widely appreciated to be a versatile polymer which could potentially be prepared from renewable resources. Due to the presence of numerous ether groups within the polymer backbone, polyglycerol is sensitive to photochemical oxidation and accordingly the material will not persist in the environment for extended periods. Furthermore, polyglycerol is hydrophilic and biocompatible, in a fashion similar to that of polyethylene glycol. Polyethylene glycol has been employed as a scaffold material for: adhesives, hydrogel wound dressings, and drug conjugation and delivery. Thus, like polyethylene glycol, polyglycerol has numerous potential applications in the pharmaceutical, biomedical, and biotechnological fields. However, unlike polyethylene glycol, polyglycerol possesses a large number of hydroxyl groups which may be chemically modified for different applications.

Despite the tremendous potential of polyglycerol, there is a dearth of synthetic methods which allow for the synthesis of high molecular weight material from inexpensive and non-toxic monomers. For example, while the preparation of high molecular weight hyperbranched polyglycerol has been previously reported, the preparation methods rely on the polymerization of a highly toxic monomer, glycidol. Glycerol, a widely available material produced as a major by-product in biodiesel synthesis, is considerably less toxic and would be an ideal monomer. However, attempts to polymerize glycerol have met with little success, and typically oligomeric glycerol materials (i.e., molecular weights less than 1,000 g/mol) are produced, such as diglycerol, triglycerol, tetraglycerol, and the like. Nevertheless, even oligomeric glycerols have found numerous applications as biodegradable surfactants, lubricants, cosmetics, and food additives.

SUMMARY

The present technology provides high molecular weight polyglycerols through an acid-catalyzed polymerization of an inexpensive, non-toxic, and renewable monomer: glycerol. The polymerization protocol described herein can be performed at modest temperatures and in a straightforward fashion using standard polymerization equipment.

In accordance with one aspect, a method of making polyglycerol is provided. The method includes heating glycerol at a temperature of at least about 110° C. at a pressure below about 400 mmHg in the absence of a glyceride and in the presence of a catalytic amount of acid selected from sulfuric acid, triflic acid, hydrochloric acid, hexafluorophosphoric acid, and tetrafluoroboric acid, or mixtures thereof.

In some embodiments, the catalytic amount of acid employed is about 1 wt % to about 5 wt %. In some embodiments, the acid is sulfuric acid. In some embodiments, the glycerol is heated under an inert atmosphere. In some embodiments, the glycerol is heated at a temperature of less than about 200° C. In some embodiments, the glycerol is heated at a temperature of about 140° C. In some embodiments the glycerol is heated at pressure at or below about 200 mmHg. In some embodiments, water is removed during the heating step. In some embodiments, the heating step is performed in the absence of an added epoxide.

In some embodiments, the method includes heating the glycerol until less than about 75 mol % of the glycerol hydroxyl groups have undergone conversion. In other embodiments, the method includes heating the glycerol until about 70 mol % to about 75 mol % of the glycerol hydroxyl groups have undergone conversion. In some other embodiments, the polyglycerol made by the method has not reached a gel point. In this regard, the heating step is performed to a point prior to reaching a critical extent of reaction ($p_c$), such as to provide polyglycerol which is not gelled. In some embodiments, the critical extent of reaction is less than or equal to about 80 mol %. In some other embodiments, the critical extent of reaction is about 70 mol % to about 80 mol %. In some embodiments, the method further includes monitoring the amount of water produced during the heating step and discontinuing heating prior to reaching the critical extent of the reaction. In some embodiments, the method further includes monitoring the conversion of glycerol to polyglycerol In some embodiments, the method provides polyglycerol with an $\overline{M}_w$, of at least 50,000 g/mol. In some embodiments, the method provides polyglycerol with an $\overline{M}_w$, from about 50,000 g/mol to about 120,000 g/mol. In some embodiments, the method provides polyglycerol with an $\overline{M}_n$ of at least 1,500 g/mol. In some embodiments, the method provides polyglycerol with an $\overline{M}_n$ from about 1,500 g/mol to about 4,000 g/mol.

The catalytic acid which remains in the polyglycerol may be removed or neutralized. Thus, in some embodiments, the method further includes neutralizing the acid with a base. In some other embodiments, the method further includes diluting the polyglycerol with water and contacting the diluted polyglycerol with an ion exchange resin. In other embodiments, the method further includes purifying the polyglycerol.

In accordance with another aspect, a method of making polyglycerol is provided, the method including heating a mixture consisting essentially of glycerol and a catalytic amount of acid selected from sulfuric acid, triflic acid, hydrochloric acid, hexafluorophosphoric acid, and tetrafluoroboric acid, or mixtures thereof, at a temperature of at least about 110° C. and a pressure below about 400 mmHg. In some embodiments, mixture consists essentially of glycerol and a catalytic amount of sulfuric acid. In some other embodiments, mixture consists of glycerol and a catalytic amount of sulfuric acid.

In accordance with another aspect, polyglycerol is provided by the methods disclosed herein. In some embodiments, a polyglycerol is provided by heating glycerol at a temperature of at least about 110° C. at a pressure below about 400 mmHg in the absence of a glyceride and in the presence of a catalytic amount of acid selected from sulfuric acid, triflic acid, hydrochloric acid, hexafluorophosphoric acid, and tetrafluoroboric acid, or mixtures thereof. In other embodiments, a polyglycerol is provided by heating a mixture consisting essentially of glycerol and a catalytic amount of acid selected from sulfuric acid, triflic acid, hydrochloric acid, hexafluorophosphoric acid, and tetrafluoroboric acid, or mixtures thereof, at a temperature of at least about 110° C. and a pressure below about 400 mmHg.

The foregoing summary is illustrative only and is not intended to be in any way limiting. In addition to the illustrative aspects, embodiments and features described above, further aspects, embodiments and features will become apparent by reference to the following drawings and the detailed description.

DETAILED DESCRIPTION

Figure 1:
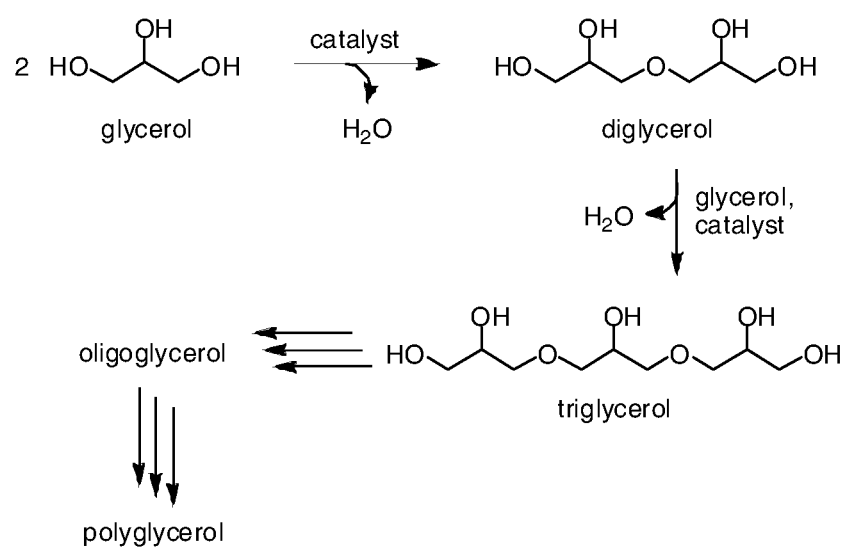
FIG. 1 is a schematic illustration of the polymerization of glycerol to polyglycerol via etherification reactions.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present technology is described herein using several definitions, as set forth throughout the specification.

As used herein, unless otherwise stated, the singular forms "a," "an," and "the" include plural reference. Thus, for example, a reference to "a cell" includes a plurality of cells, and a reference to "a molecule" is a reference to one or more molecules.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

In one aspect a method of making polyglycerol is provided by the present technology. The method includes heating glycerol at reduced pressure in the presence of a catalytic amount of acid and in the absence of a glyceride to form polyglycerol.

FIG. 1 illustrates a simplified depiction of a catalytic polymerization of glycerol to polyglycerol. Such a polymerization reaction may be performed with standard laboratory glassware, such as that described in the Examples. The polymerization reaction may be performed under an inert atmosphere. As used herein, the term "inert atmosphere" means an atmosphere which does not react with any of the reactants, intermediates, or end products, or otherwise interfere with the reaction. Typically, the polymerization reaction will be performed in an inert atmosphere of nitrogen or argon as to minimize the possibility of glycerol oxidation (or the oxidation of any other reactants), as well as to minimize the possibility of oxidation of the polyglycerol.

Strong protic acids are effective in catalyzing the polymerization of glycerol. Non-limiting examples of such acids include sulfuric acid ($H_2SO_4$), triflic acid ($CF_3SO_3H$) hydrochloric acid (HCl), hexafluorophosphoric acid ($HPF_6$), and tetrafluoroboric acid ($HBF_4$). The acids may be used in pure form or as a solution, such as an aqueous solution. While a mixture of multiple acids may be employed, the polymerization reaction proceeds efficiently with a single acid. The catalytic amount of acid used will vary, depending upon the desired rate of polymerization. In general, an appreciable rate of polymerization will be achieved when the catalytic amount of acid is at least 0.1 wt %. In some embodiments, the catalytic amount of acid is about 1 wt % to about 5 wt %. In other embodiments, the catalytic amount of acid is about 1 wt % to about 10 wt %. Examples of catalytic amounts of acid that may be used include about 0.1 wt %, about 0.2 wt %, about 0.5 wt %, about 0.8 wt %, about 1 wt %, about 1.5 wt %, about 2 wt %, about 2.5 wt %, about 3 wt %, about 3.5 wt %, about 4 wt %, about 4.8 wt %, about 5.5 wt %, about 6.0 wt %, about 6.5 wt %, about 7 wt %, about 7.5 wt %, about 8 wt %, about 8.5 wt %, about 9 wt %, about 9.5 wt %, about 10 wt %, and ranges between any two of these values. In one embodiment, the acid is sulfuric acid and the catalytic amount of sulfuric acid is about 4.8 wt %. While higher weight percentages of acid may be used (i.e., higher than 10 wt %), the polymerization reaction may be difficult to control, resulting in the formation of by-products and low molecular weight polyglycerol.

The polymerization of glycerol is performed at a temperature to achieve a reasonable polymerization rate, such as to polymerize the glycerol in a period of less than about 24 hours. Typically, such a polymerization rate may be obtained by heating the glycerol in the presence of the catalytic acid at a temperature of at least about 110° C. In some embodiments, the temperature is less than about 200° C. Examples of temperatures that may be used include about 110° C., about 120° C., about 130° C., about 140° C., about 150° C., about 160° C., about 170° C., about 180° C., about 190° C., about 200° C., and ranges between any two of these values. While the glycerol may be heated at higher temperatures, i.e., higher than 200° C., the polymerization reaction may be difficult to control and by-products and charring may develop. Furthermore, heating the glycerol at such higher temperatures may result in the formation of low molecular weight oligomeric glycerol products and decomposition of polyglycerol.

The glycerol and catalytic amount of acid are heated at a reduced pressure to form the polyglycerol. The use of reduced pressure allows for continuous removal of a by-product of the reaction: water. By removing water during the heating step, the polymerization reaction may be driven towards completion. The pressure inside the reaction vessel where the polymerization reaction is performed will typically be below about 400 mmHg (~53.3 kPa). In some embodiments the pressure is at or below: about 350 mmHg, about 300 mmHg (~40.0 kPa), about 250 mmHg, about 200 mmHg, about 150 mmHg, about 100 mmHg, about 50 mmHg, about 25 mmHg, and ranges between any two of these values. Pressures lower than about 200 mmHg may result in evaporation of the glycerol monomer from the reaction vessel. In such an instance, fresh glycerol may be added to the polymerization reaction at a rate similar to that at which glycerol is being evaporated. Alternatively, the reaction vessel may be equipped with a recycling system to collect and reuse evaporated glycerol monomer. For example, the evaporated glycerol may continuously be condensed, collected, optionally purified (such as by distillation to remove water), and recharged to the reaction vessel. Finally, the polymerization may be performed while heating both under an inert atmosphere and under reduced pressure.

The glycerol and catalytic amount of acid are heated in the absence of a glyceride. As used herein, the term "glyceride" refers to all mono-, di-, and tri-acylglycerols of the formula $(RC(O)O)_n C_3H_5(OH)_{3-n}$, where n is 1, 2, or 3, and R is any organic group having from 1 to 30 carbon atoms. Examples of glycerides include triacetin, glyceryl 1,3-distearate, glyceryl trioctanoate, rac-1-monopalmitoleoyl glycerol, glyceryl 1-myristate, and the like.

The glycerol and catalytic amount of acid may also be heated in the absence of an added epoxide; i.e., no exogenous epoxide is added to the glycerol and catalytic amount of acid. The term "epoxide" refers to an unsubstituted or substituted oxirane. Substituted oxiranes include monosubstituted oxiranes, disubstituted oxiranes, trisubstituted oxiranes, and tetrasubstituted oxiranes. Non-limiting examples of epoxides include ethylene oxide, propylene oxide, cycloheptene oxide, styrene oxide, epichlorohydrin, glycidol, 2-bromo-3-methyloxirane, cis-2-methyl-3-propyloxirane, 2,3-dimethyl-2,3-epoxybutane, bisphenol A diglycidyl ether, glycidyl trityl ether, 3,4-epoxy-1-butene, 3,3,3-trifluoro-1,2-epoxypropane, tetracyanoethylene oxide, glycidamide, epoxomicin, and the like.

The glycerol and catalytic amount of acid may also be heated in the absence of a carboxylic acid of the formula $RCO_2H$, where R is any organic group having from 1 to 30 carbon atoms. Examples of such carboxylic acids include acetic acid and fatty acids.

At later stages of the polymerization reaction, cross-linking of the polyglycerol may occur. Eventually, at the critical extent of reaction, $p_c$, the gel point (i.e., the moment when an infinite polymer network first appears) will be reached, and gelation will occur. When the polyglycerol passes the gel point, the polymer becomes a gel and loses its fluidity. Accordingly, such a gel can be difficult to remove from the reaction vessel. Thus, for reasons of practicality, it may be desired to terminate the polymerization reaction prior to the gel point. Termination of the reaction may be accomplished by removing the reaction vessel from the heat source. The reaction may also be terminated by neutralization of the catalytic acid, such as by the addition of a base. Suitable bases include, but are not limited, sodium hydroxide and sodium carbonate. The addition of base may be coupled with cooling the reaction mixture, as to avoid excess heat generation during the acid-base neutralization. As shown in the Examples, $p_c$ may be measured experimentally or calculated for the polymerization of glycerol with good accuracy. In some embodiments, the critical extent of reaction is less than or equal to about 80 mol %. In some other embodiments, the critical extent of reaction is about 70 mol % to about 80 mol %.

The progress of the polymerization reaction may be monitored in a variety of ways as to avoid reaching the critical extent of reaction, and thus gel formation. The polymerization reaction may be monitored continuously, or may be monitored periodically, such as about every 5 minutes, about every 10 minutes, about every 15 minutes, about every 20 minutes, about every 30 minutes, about every 45 minutes, about every 1 hour, about every 90 minutes, about every 2 hours, about every 3 hours, about every 4 hours, about every 5 hours, about every 6 hours, about every 7 hours, about every 8 hours, or about every 10 hours. For example, the polymerization reaction progress may be determined from the amount of water formed during the reaction. In this case, the water formed during the polymerization reaction can be collected (such as by condensing it into a Dean-Stark trap for a laboratory scale polymerization or by condensing it into a separate vessel in the case of a large scale polymerization), the quantity of water determined, and the molar percent of the glycerol hydroxyl groups that have undergone conversion calculated. By "conversion", it is meant that the glycerol hydroxyl groups are transformed into ether linkages in the polyglycerol and this transformation occurs with the release of molecules of water. For polymerization reactions performed on a large scale, such as those performed in a commercial reactor, it may be desirable to continuously monitor the reaction in real time. This may be accomplished through continuous FT-IR or Raman spectroscopic analysis of the polymerization mixture using equipment known in the art (e.g., a ReactIR instrument available from Mettler-Toledo, Columbus, Ohio). In particular, as the polymerization proceeds (and water is removed from the polymerization mixture), there will be a reduction in the intensity of the O—H stretching signal in the IR or Raman spectrum which can be quantified and correlated to the conversion of glycerol hydroxyl groups. In some embodiments, the present method includes heating the glycerol until less than about 75 mol % of the glycerol hydroxyl groups have undergone conversion. In other embodiments, the method includes heating the glycerol until about 70 mol % to about 75 mol % of the glycerol hydroxyl groups have undergone conversion.

The molecular weight of the polyglycerols made by the present method may be tailored by adjusting the reaction conditions during the heating step, such as temperature and heating time. It has been observed that the use of temperatures greater than 200° C. results in the formation of lower molecular weight polyglycerol and/or oligomeric polyglycerols. Side reactions may occur at temperatures greater than 200° C., such as the generation of cyclic compounds. As detailed in the Examples below, non-gelled, high molecular weight polyglycerols may be obtained through monitoring and controlling monomer conversion during the polymerization.

In some embodiments, the polyglycerol has a weight-average molecular weight ($\overline{M}_w$) at least 40,000 g/mol, or at least 50,000 g/mol. In some embodiments, the polyglycerol has an $\overline{M}_w$ from about 50,000 g/mol to about 120,000 g/mol. In some embodiments, the polyglycerol has a number-average molecular weight ($\overline{M}_n$) of at least 1,500 g/mol. In some embodiments, the polyglycerol has an $\overline{M}_n$ from about 1,500 g/mol to about 4,000 g/mol.

The polyglycerols prepared by the present methods may optionally be purified by a number of methods. For example, the method may further include diluting the polyglycerol with water and contacting the polyglycerol with an ion exchange resin to remove the catalytic amount of acid. Any suitable ion exchange resin may be employed and the selection of a given resin is an engineering decision based upon exchange capacities, flow rates, and other factors affecting the cost of operation. Non-limiting examples of ion exchange resins which may be used include Amberlyst A26 OH resin (a strongly basic hydroxide-containing anionic exchange resin available from The Dow Chemical Company, Midland, Mich.) and Lewatit MP 62 WS (a weakly basic hydroxide-containing anion exchange resin available from Lanxess, Leverkusen, Germany). The residual catalytic acid in the polyglycerol may also be neutralized by adding a base, including but not limited to, a base such as sodium hydroxide or sodium carbonate. Furthermore, the polyglycerols prepared by the present methods may exposed to a variety of absorbents known in the art to remove traces of acid, colored impurities, low molecular weight impurities, etc., followed by filtration. Non-limiting examples of absorbents include, molecular sieves, activated carbon, diatomaceous earth, calcium carbonate, silicas, alumina, silicalumina, Perlite, and various types of clay (e.g., Fuller's earth). To reduce viscosity and thus aid in filtration, the polyglycerols may be optionally diluted with a solvent (e.g., water) prior to exposure to an absorbent.

As will be appreciated by those of skill in the art, the methods described herein may be modified in a number of ways. For example, the glycerol and the catalytic amount of acid may be dissolved in a solvent prior to the heating step. In this manner, the rate of polymerization may be further controlled by monomer dilution. The solvent may be a hydrophilic solvent. Examples of hydrophilic solvents include, but are not limited to, water, methanol, ethanol, 1-propanol, 2-propanol, n-butanol, sec-butanol, tert-butanol, dimethyl sulfoxide, dimethylformamide, acetone, 2-butanone, and acetonitrile. Additionally, the glycerol monomer may be purified prior to use in the polymerization reaction, such as by distillation.

The present technology, thus generally described, will be understood more readily by reference to the following Example, which is provided by way of illustration and is not intended to be limiting of the present technology.

EXAMPLE

Polyglycerol Syntheses

All chemicals were purchased from Sigma-Aldrich Canada Ltd. (Oakville, ON) and used without further purification. All polymerizations were performed under continuous sparging of nitrogen to prevent oxidation of the glycerol during the polymerization. Polymerizations were carried out in a 1 L glass reactor equipped with a distillation trap topped with a condenser, a nitrogen inlet, a catalyst feeding and sampling port, a temperature probe, and a mechanical stirrer. The stirring speed (250 rpm) and the temperature were controlled separately. Polyglycerol was synthesized by step-growth etherification of glycerol in the presence of various catalysts at varying temperatures. Since glycerol polymerization at atmospheric pressure tends to be slow, a vacuum pump was attached to the reactor through the condenser and the condensation reaction was carried out at pressures below 26 kPa (~200 mmHg absolute). A Dean-Stark trap topped by a condenser was attached to the reactor to continuously remove water from the reaction mixture. The reaction progress was determined by monitoring the water formation in the distillation trap. Complete, or near complete, conversion of glycerol monomer was favored in this Example by removing the volatile by-product, water.

Polyglycerol Purification and Catalyst Removal

No attempt was made to remove residual catalyst from the polyglycerol samples. For polyglycerols containing acid catalyst, the catalyst may be neutralized by addition of a base, such as sodium hydroxide or sodium bicarbonate. Alternatively, residual acid may be removed by dissolving the polyglycerol in an equal amount of water to provide a diluted polyglycerol (and thus a lower viscosity material), and passing the diluted polyglycerol through an ion exchange resin, such as Amberlyst A26 OH resin (a strongly basic hydroxide-containing anion exchange resin, available from The Dow Chemical Company) or Lewatit MP 62 WS (a weakly basic hydroxide-containing anion exchange resin available from Lanxess). Rather than passing the diluted polymer through an ion exchange resin, the ion exchange resin may be added directly to the diluted polymer, the mixture stirred or shaken, and the resin removed by filtration. After exposure to the ion exchange resin, the diluted and purified polyglycerol may then be placed under vacuum to remove water. Gentle heating may also be employed, for example, heating at or below a temperature of about 140° C.

Polyglycerol Characterization

A Waters Gel Permeation Chromatograph (GPC) was utilized for the measurement of the polymer molecular weight and its distribution. The GPC system consists of a Waters 501 HPLC pump, a Waters R401 differential refractometer, and a VARIAN PL aquagel-OH column. Water, the mobile phase, was running at 1 mL/min. The injection volume was 20 µL for each sample and all samples were dissolved in water and filtered through a 0.45 µm disposable membrane filter (Millipore) prior to injection. Polyethylene glycol standards (VARIAN Inc.) were used to construct the calibration curve. The data were processed using Breeze™ software provided by Waters.

The Mark-Houwink equation, $[\eta]=KM^\alpha$, relates polymer molecular weight, M, to intrinsic viscosity, $[\eta]$. The calculated values for the Mark-Houwink parameters K and $\alpha$ (0.0002 $cm^3 \cdot g^{-1} \cdot mol^{-1}$ and 0.75 respectively) were determined from glycerol as well as low molecular weight polyglycerol standards from Solvay Chemicals with known molecular weights and narrow molecular weight distributions.

NMR spectra were recorded on a Bruker Avance 500 MHz NMR spectrometer. The analyses were carried out in deuterated dimethylsulfoxide, DMSO-$d^6$ (with tetramethylsilane) solutions at a concentration of ~2% w/v. The deuterated NMR solvent was used as both the solvent and the reference.

Gel content of the polyglycerol samples were analyzed using the membrane gel partitioning method. In this method, about 600 to 800 mg of 100% solid polymer was weighed onto a polyvinylidene fluoride (PVDF) Millipore membrane disk of 5 µm porosity. The disk was heat sealed and transferred to a scintillation vial. About 20 mL of water was added to the vial and placed in a shaker for 16 to 24 h. The sealed disk was then removed, washed with water, and dried first by placing it on a Whatman No. 1 filter paper. The dried disk was weighed and the insoluble portion of the polymer determined by Equation 1:

$$\text{percent insoluble} = \frac{(b-c)}{a} \times 100 = \% \text{ gel} \quad (1)$$

where $\alpha$ is the total weight of 100 percent solids polymer, b is the weight of the polymer plus membrane before water treatment, and c is the polymer plus membrane remaining after water treatment.

Effect of Temperature

In general, the reaction temperature was kept below 200° C. to avoid: evaporation of the glycerol monomer (boiling point=290° C.); degrading the polyglycerol product; and any undesired side reactions such as acrolein formation. Several polymerizations were carried out at temperatures ranging from 100 to 180° C. Heating the reaction mixture at temperatures at or below ~120° C. resulted in some glycerol polymerization; however, the reaction rate was very slow (e.g., at 120° C., conversion of glycerol OH groups was ~30 mol % after 600 min using 1.2 wt % sulfuric acid catalyst).

Effect of Catalyst

The polymerization of glycerol was investigated using acidic and basic catalysts, including mineral and organic acids, as well as inorganic hydroxides and carbonates. The catalysts were chosen on the basis of their activity at elevated temperatures and their good thermal stability. Table 1 indicates the reaction conditions along with conversion and average molecular weight results for each run.

TABLE 1

Conversion and molecular weight data for polymerization of glycerol at 140° C. using different types and concentrations of catalysts.

| Catalyst | Catalyst Concentration (wt %) | Time (min) | Conversion of glycerol OH groups (mol %) | $\overline{M}_w$ (g/mol) | $\overline{M}_n$ (g/mol) | Average number of monomer units[‡] |
|---|---|---|---|---|---|---|
| Ca(OH)$_2$ | 1.2 | 400 | 10 | 113 | 100 | ~1.5 |
| Ca(OH)$_2$ | 2.4 | 360 | 12 | 124 | 106 | ~1.7 |
| CaCO$_3$ | 2.4 | 400 | 11 | 104 | 95 | ~1.4 |
| CaCO$_3$ | 1.2 | 420 | 7 | 100 | 93 | ~1.4 |
| H$_2$SO$_4$ | 1.2 | 445 | 40 | 720 | 160 | ~9.7 |
| H$_2$SO$_4$ | 3.6 | 360 | 71 | 95,600 | 2,700 | ~1300 |
| H$_2$SO$_4$ | 4.8 | 240 | 72 | 111,400 | 3,600 | ~1500 |
| p-TsOH* | 1.2 | 580 | 40 | 160 | 140 | ~2.2 |

*p-toluenesulfonic acid.
[‡]$\overline{M}_w$ divided by the glycerol monomer repeat unit (74 g/mol).

Figure 2:
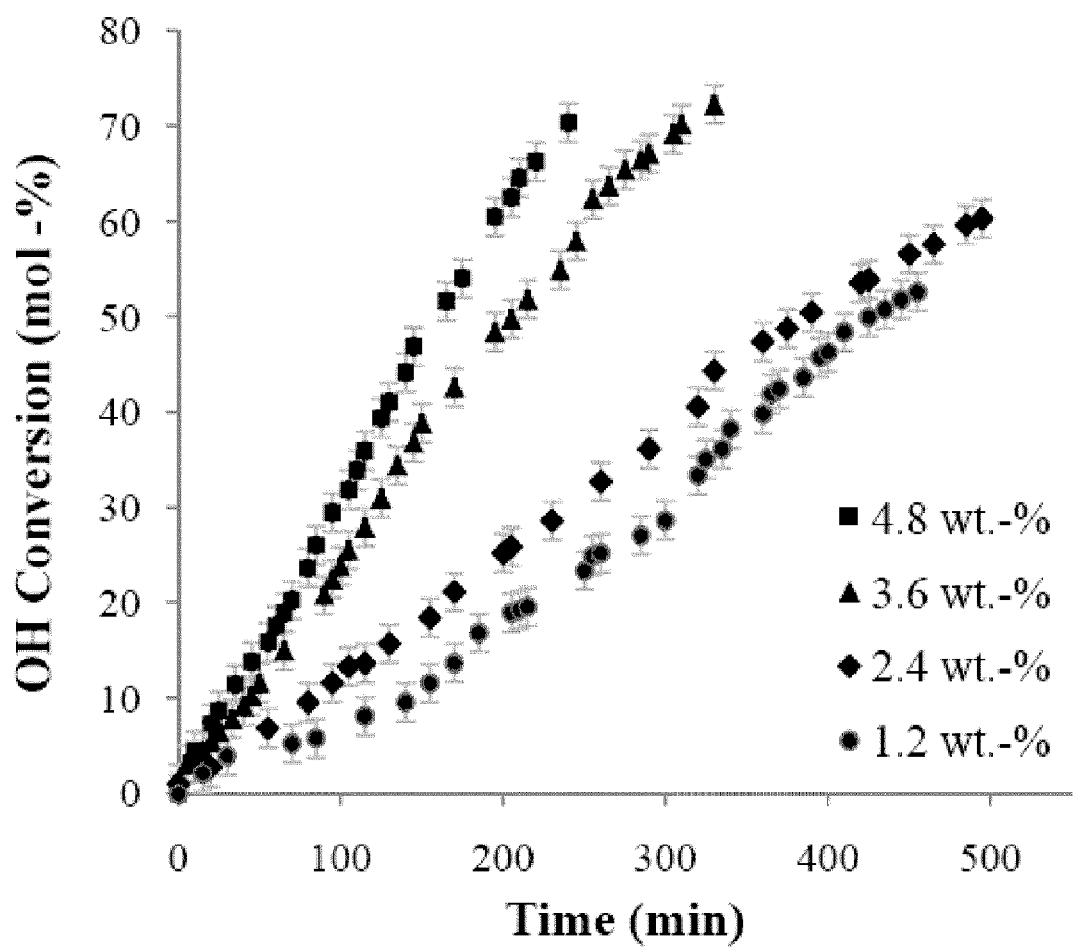
FIG. 2 is a graph depicting conversion of hydroxyl groups (mol %) at various times for the polymerization of glycerol using sulfuric acid catalyst at concentrations of 1.2 wt %, 2.4 wt %, 3.6 wt %, and 4.8 wt %.

As shown in Table 1, the conversion of glycerol hydroxyl groups and the molecular weight of the polyglycerol were greatly influenced by the type of catalyst employed. The polymerization of glycerol proceeded fastest with sulfuric acid as catalyst as indicated by the highest observed conversion of monomer hydroxyl groups along with the highest molecular weights. A comparison of polymerization rates using different concentrations of sulfuric acid catalyst is shown in FIG. 2. Faster conversions of hydroxyl groups were observed using higher concentrations of sulfuric acid. In the case sulfuric acid catalyst at 4.8 wt % loading, exceptionally high weight-average molecular weights were obtained after 240 minutes, corresponding to a polymer with approximately 1,500 glycerol units on average. Furthermore, deconvolution of the GPC trace for polyglycerol produced after 240 minutes with 4.8 wt % sulfuric acid, revealed that the first eluting fraction (~1% of the total polymer) had an $M_w$ of 232,900 g/mol and an $M_n$ of 204,100 g/mol, corresponding to a polyglycerol averaging more than 3,100 monomer units (see FIG. 5, fraction eluting at a retention time of ~5 minutes which appears as a shoulder to the peak to the right). Results showed that the catalyst concentration had no significant effect on microstructure of the polymer samples which were taken at the same hydroxyl conversions. The material obtained using p-toluenesulfonic acid as a catalyst had a much lower weight-average molecular weight than the corresponding material obtained using sulfuric acid at similar concentration (i.e., 1.2 wt %) and hydroxyl conversion (i.e., 40%). Furthermore, in contrast to sulfuric acid as a catalyst, increases in p-toluenesulfonic acid catalyst concentration above 1.2 wt % did not provide the high molecular weight polyglycerol; similarly low molecular weights were observed.

Figure 3:
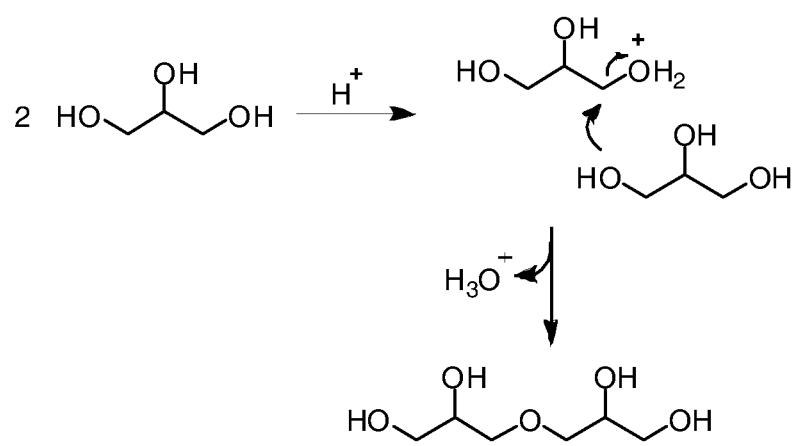
FIG. 3 is a schematic illustration of the acid-catalyzed reaction mechanism of the dimerization of glycerol proceeding through an $S_N 2$ mechanism.

The efficiency of catalysts based on the rates of polymerizations was (from highest to lowest): sulfuric acid (H$_2$SO$_4$) >p-toluenesulfonic acid (p-TsOH)>calcium hydroxide (Ca(OH)$_2$)>calcium carbonate (CaCO$_3$). Without wishing to be bound by any particular theory, it is believed that the difference in polymerization rates may be due to different polymerization mechanisms, depending on the nature of the catalyst employed. In particular, as a strong protic acid, sulfuric acid is expected to catalyze the polymerization reaction by protonation the primary alcohol of glycerol rendering a good leaving group (i.e., water, see FIG. 3). The reaction may proceed by an $S_N1$-type pathway, where the H$_2$O leaves before the attack occurs, by an $S_N2$-type pathway, where the $^+$H$_2$O—C bond is still intact (shown in FIG. 3), or by a combination of such pathways.

Figure 4:
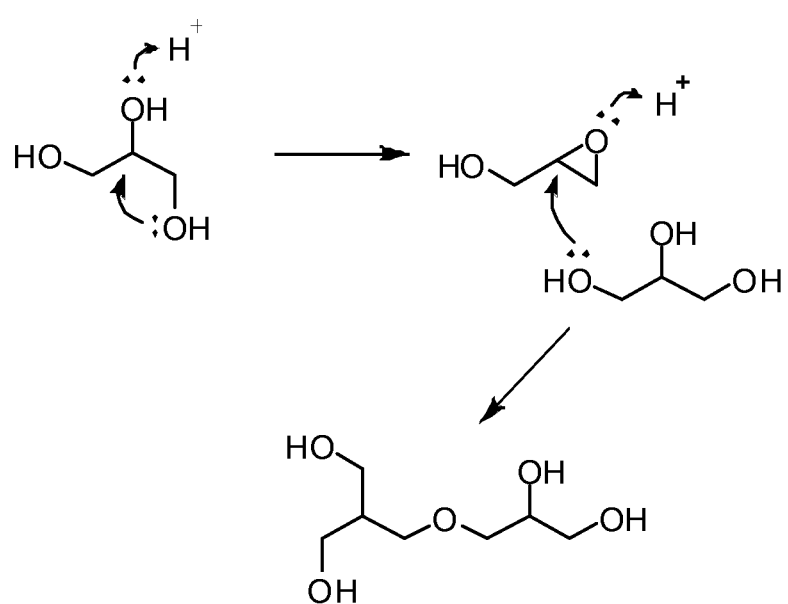
FIG. 4 is a schematic illustration of the acid-catalyzed reaction mechanism of the dimerization of glycerol proceeding through an epoxide intermediate.
Figure 6:
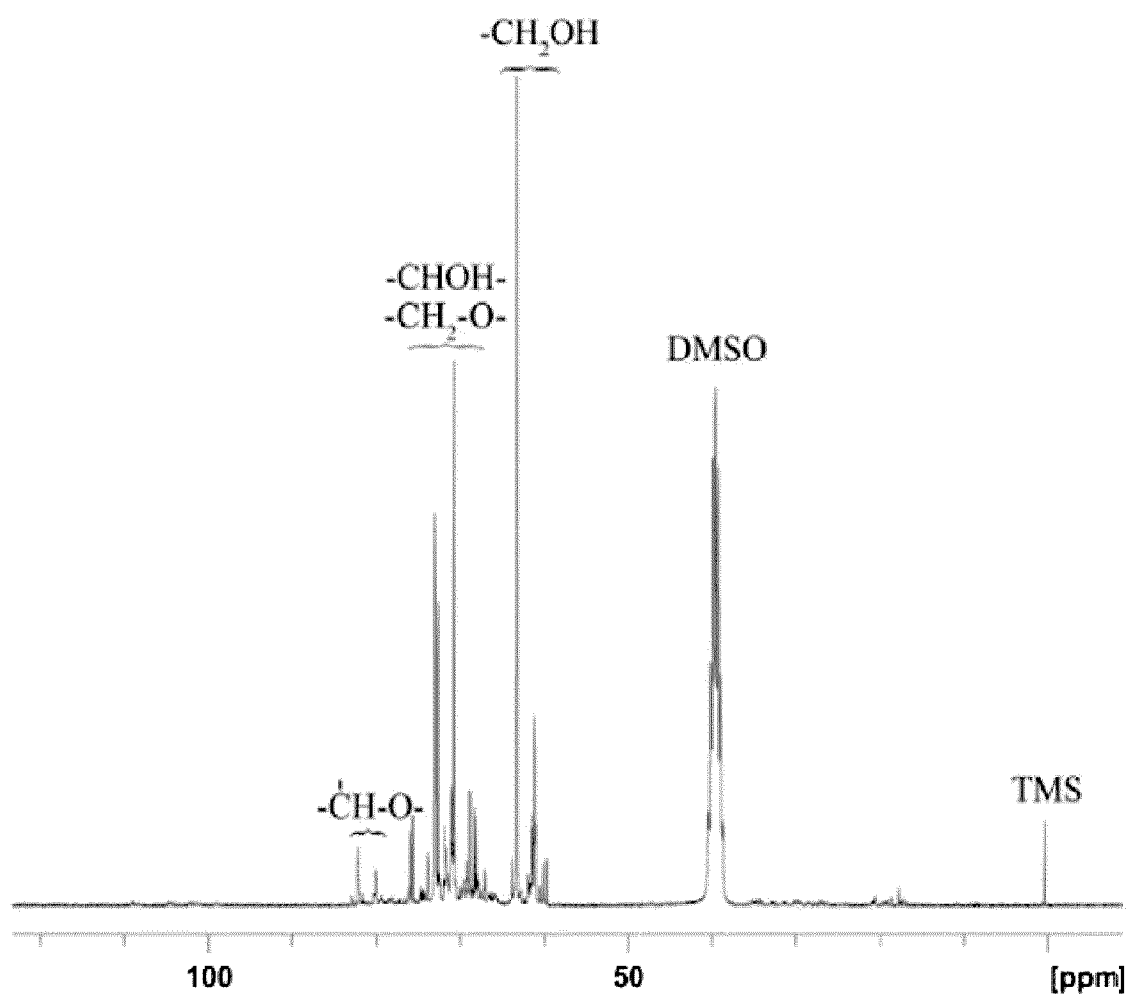
FIG. 6 is the $^{13}C$ NMR spectrum of polyglycerol in DMSO-$d^6$ prepared by polymerizing glycerol in the presence of 3.6 wt % $H_2SO_4$ at 140° C. for 360 minutes.

Performing the reaction at elevated temperatures may result in the formation of small amounts of glycidol, a reactive epoxide which may further react with glycerol after acid activation. The acid-catalyzed opening of glycidol likely takes place at the most substituted carbon as indicated in FIG. 4, leading to some branching of the polyglycerol. The presence of tertiary carbons within the polyglycerol was confirmed by $^{13}$C NMR spectroscopy (FIG. 6). Thus, it is possible that small concentrations of glycidol are formed and consumed under the reaction conditions at 140° C. Temperatures greater than 140° C. may result in higher concentrations of glycidol, and thus, potentially more branching within the polyglycerol.

Polyglycerol obtained by the self-condensation of glycerol in the presence of sulfuric acid is a mixture of polyols with linear, branched and cyclic structures of different degrees of polymerization with high functionality. The predominant species are linear polyglycerols, along with a lesser amount of branched polyglycerols, as evidenced by $^{13}$C NMR spectroscopy studies (FIG. 6). Branched polyglycerols may have been formed according to the proposed epoxide reaction mechanism illustrated in FIG. 4 or by reactions with secondary hydroxyl groups. Cyclic products may have resulted from intramolecular ring closure reactions. The content of branched and cyclic structures in polyglycerol became more evident at higher extents of polymerization. Catalyst concentration had no obvious impact on the degree of branching. Nevertheless, despite the presence of some non-linear polymers, polyglycerol could be prepared with very high molecular weights.

Predicting the Gel Point and Critical Extent of Reaction

The polymerization of glycerol, with an average functionality (f) greater than two, may not only lead to branching but also to a cross-linked polymer structure. Such cross-linking may eventually lead to gelation. At the moment when an infinite polymer network first appears, i.e., at the gel point, the polymerization system loses its fluidity, which can be identified by the failure of nitrogen bubbles to rise through the reaction mixture. From a practical point of view, it is desirable to predict the extent of reaction at the gel point (i.e., the critical extent of reaction, $p_c$) in order to stop the polymerization prior to that point and avoid gelation for straightforward removal from the reaction vessel.

The critical extent of reaction, $p_c$, may be estimated starting from Equation 2, the Carothers equation:

$$p = \frac{2}{f_{av}} - \frac{2}{\overline{X}_n f_{av}} \quad (2)$$

where p is the conversion, $f_{av}$ is the average number of functional groups per molecule in the reaction mixture, and $\overline{X}_n$ is the number-average degree of polymerization. The critical extent of reaction, $p_c$, will be reached at the gel point when the number-average degree of polymerization becomes infinite. Thus, at the gel point, the Equation 2 reduces to Equation 3, which can be used to calculate the conversion of functional groups required to reach the onset of gelation:

$$p_c = \frac{2}{f_{av}} \quad (3)$$

Thus, for a homopolymerization of glycerol, a trifunctional monomer, the calculated critical extent of reaction is approximated to be 0.67 (i.e., $f_{av}$ is 3).

Another approach for estimating $p_c$ for the homopolymerization of a multifunctional monomer involves branching theory developed by Flory and Stockmayer. In particular, gelation is assumed to occur when the weight-average degree of polymerization, $\overline{X}_w$, reaches infinity according to Equation 4:

$$\overline{X}_w = \frac{(1+p)}{1-p(f-1)} \quad (4)$$

Where p is the conversion and $f$ is the functionality of the branch unit. Thus, the critical extent of reaction, occurs when $1 > p(f-1)$; reducing Equation 4 to Equation 5:

$$p_c = \frac{1}{1-f} \quad (5)$$

In the case of glycerol, $f$ is 3, and thus, $p_c$ is approximated to be 0.50.

Samples collected during the polymerization were analyzed for gel content using the membrane gel partitioning method. No gel was detected up to a conversion of 72±3% of the glycerol hydroxyl functional groups. Thus, the predicted values for $p_c$ are reasonably close to the experimental values. Differences between the predicted and experimental values may be ascribed to the failure of certain assumptions present inherent in Equations 3 and 5, such as: (i) the assumption that the reactivity of all glycerol hydroxyl groups are the same and is independent of chain structure (e.g., degree of branching, degree of polymerization, presence of isomers, etc.) and (ii) that no intramolecular reactions occur between functional groups on the same molecule. In the case of (ii) such reactions would consume the functional groups normally expected to generate cross-links and polymerization would need to be carried out to a greater extent to reach the gel point. Nevertheless, both numerical computation and experimental data clearly indicate that as the gel point (critical extent of reaction) is approached; reactant concentrations decrease and larger polymer chains are formed, which have a higher tendency to react intramolecularly.

Figure 5:
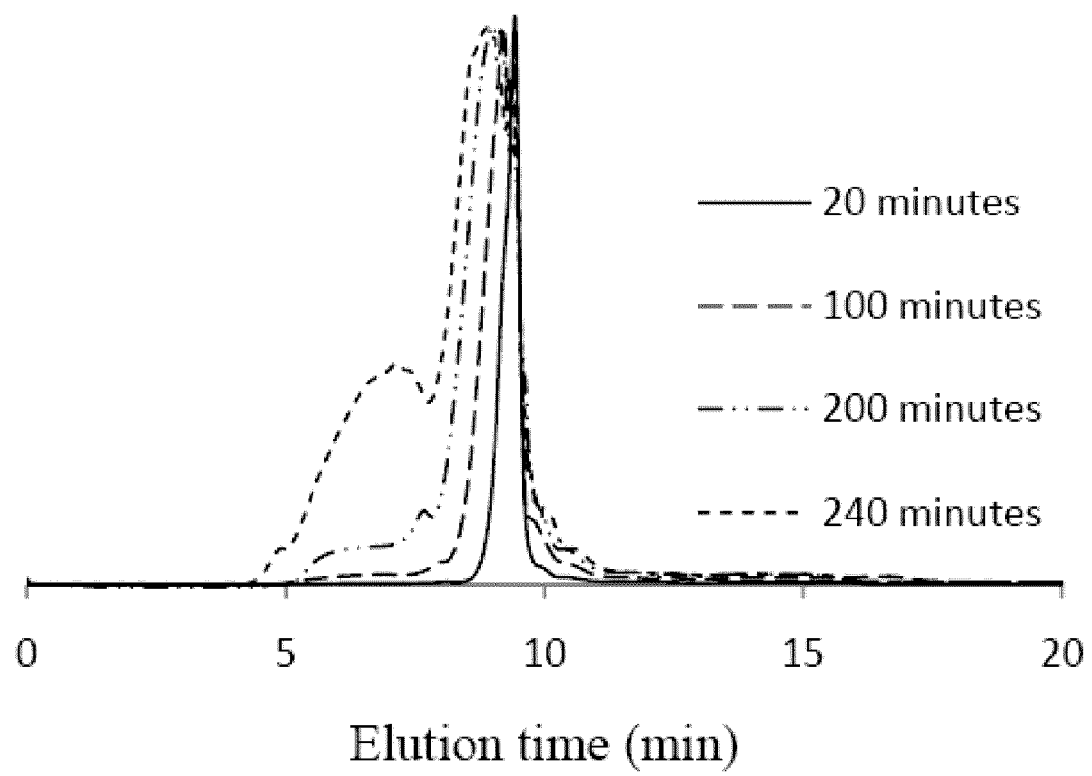
FIG. 5 shows stacked GPC elution curves of polyglycerol produced using 4.8 wt % of sulfuric acid catalyst, after 20 minutes, 100 minutes, 200 minutes, and 240 minutes.

Multimodal molecular weight distributions were observed for all samples. Both number-average molecular weights ($\overline{M}_n$) and weight-average molecular weights ($\overline{M}_w$) showed an increase with reaction time. An overlay of GPC data of polyglycerol samples obtained from a run with 4.8 wt % sulfuric acid catalyst is shown in FIG. 5. The increase in the width of the curves indicates that the polydispersity increased as the reaction progressed. FIG. 5 further indicates that larger polymers are formed as reaction time increases (i.e., shorter elution times in GPC trace).

Average molecular weights for the polyglycerol samples were calculated by deconvolution of the multimodal peaks using the GPC software. $\overline{M}_w$, and $\overline{M}_n$ were determined using Equations 6 and 7 respectively:

$$\overline{M}_w = \frac{(1+p)}{1-p(f-1)}\left(M_0 - \frac{fM_c}{2}\right) + \frac{(1-p)fM_c/2}{1-p(f-1)}\left[1 - p\frac{(M_0 - M_c)}{M_0 - fM_c/2}\right] \quad (6)$$

$$\overline{M}_n = \left(M_0 - \frac{fp}{2}M_c\right) / (1 - fp/2) \quad (7)$$

Where $M_0$ is the monomer molecular weight of glycerol (92 g/mol), and $M_c$ is the molecular weight of the condensate, water (18 g/mol). Since the experimental gel point and high molecular weights were observed at 74±3 mol % conversion (Table 2), it was expected that $f$ be less than 3 for the polyglycerol system. The calculated value for $f$ was determined by employing the $\overline{M}_w$ values obtained through GPC measurements in Equation 6. As shown in Table 2, the calculated value for $f$ was approximately 2.4 for the high molecular weight samples. Using the statistical method and the estimated $f$ value of 2.4, the gel point can be predicted to be at ~71 mol % conversion of hydroxyl groups; fairly close to the experimentally observed critical conversion in Table 2.

As can be seen from the GPC elution curves (FIG. 5) polymer chains are growing during the reaction and long chains are not only formed close to the gel point (as the model foresees) but at earlier levels of monomer conversion. Nonetheless, chain growth is very fast close to the critical point and it is important to stop the reaction prior to gelation.

TABLE 2

Experimental results and model predictions from reactions using sulfuric acid catalyst.

| | Catalyst Concentration (wt %) | | |
|---|---|---|---|
| | 1.2 | 3.6 | 4.8 |
| Conversion of OH groups (mol %) | 73 | 71 | 72 |
| $\overline{M}_w$ | 58,000 | 95,600 | 111,400 |
| $\overline{M}_n$ | 2,000 | 2,700 | 3,600 |
| Predicted glycerol functionality (f) from Equation 5 | 2.37 | 2.40 | 2.39 |
| Predicted critical conversion of hydroxyl groups ($p_c$, mol %) from Equation 4 using predicted f | 72.9 | 71.4 | 71.9 |
| Observed critical conversion ($p_c$, mol %) | 77 | 76 | 74 |
| Predicted $\overline{M}_n$ from Equation 7 using predicted f | 560 | 520 | 550 |

Figure 7:
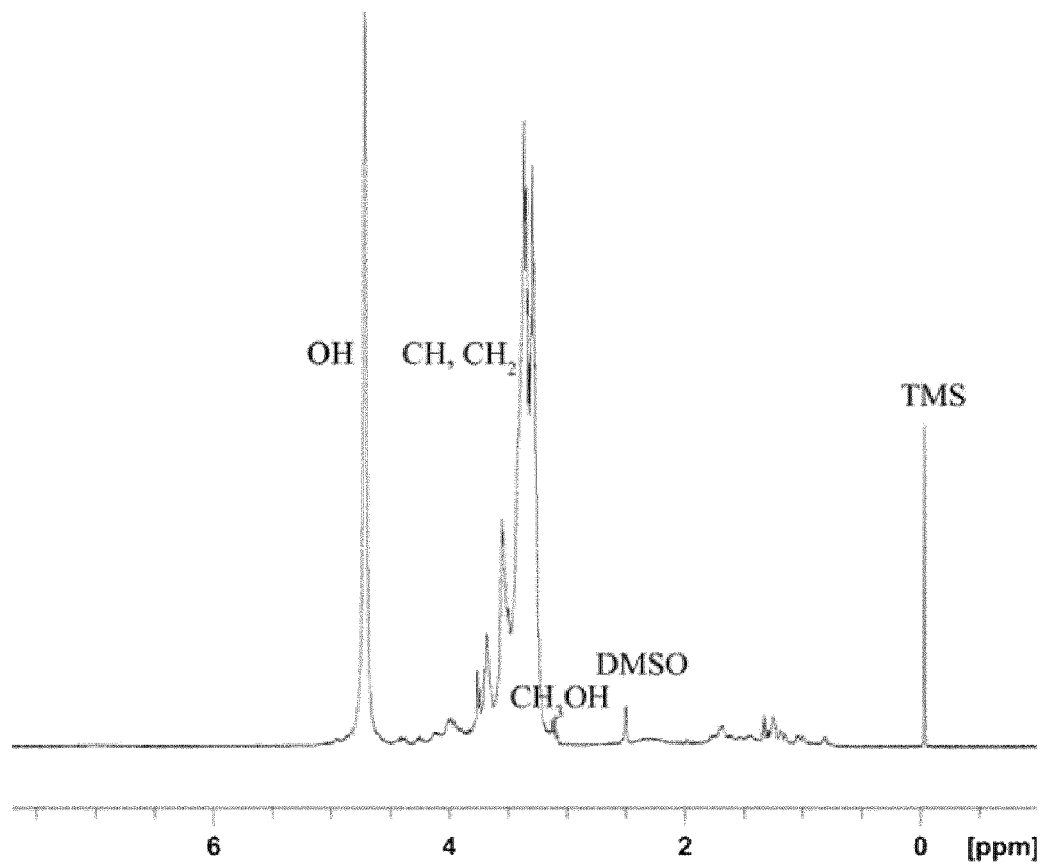
FIG. 7 is the $^1H$ NMR spectrum of polyglycerol in DMSO-$d^6$ prepared by polymerizing glycerol in the presence of 3.6 wt % $H_2SO_4$ at 140° C. for 360 minutes.

NMR Spectral Analysis of Polyglycerol $^{13}$C NMR and $^1$H NMR spectra of a polyglycerol sample are indicated in FIGS. 6 and 7, respectively. The chemical shifts of the carbon and hydrogen atoms were established on the basis of oligoglycerol standards and previously reported assignments for hyperbranched polyglycerol. In the $^1$H NMR spectrum, the methylene and methine protons of polyglycerol appeared as a broad resonance pattern between 3.2 and 4.1 ppm and hydroxyl proton signals were observed around 5 ppm. In the $^{13}$C NMR spectrum, signals in different regions were assigned as follows: —CH$_2$OH carbons of end groups in 60 to 64 ppm, —CHOH— carbons at 68 to 73 ppm, —CH$_2$—O— carbons at 72 to 75 ppm and —CH—O carbons at 79 to 82 ppm region. The presence of a small amount of branched structures is supported by the $^{13}$C NMR spectra as observed by the repeating resonances at 79 to 82 ppm region. Additionally, an appearance of some weak signals was observed in the 0.75 to 2.5 ppm region in the $^1$H NMR spectra and in the 15 to 20 ppm region in the $^{13}$C NMR spectra. In order to investigate the connectivity of different regions, heteronuclear two-dimensional correlation spectroscopy (HETCOR) experiments were performed. Assignment of the carbon nuclei with protons attached was made and the results indicated that the above mentioned weak proton signals correlates to weak upfield carbon signals. These signals were observed in samples from higher monomer conversions and can be assigned to CH$_2$ and CH$_3$ groups in different cyclic products previously proposed for oligoglycerol.

Equivalents

The embodiments, illustratively described herein may suitably be practiced in the absence of any element or elements, limitation or limitations, not specifically disclosed herein. Thus, for example, the terms 'comprising,' 'including,' 'containing,' etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Similarly, the phrase "at least about" some value such as, e.g., wt % includes at least the value and about the value. For example "at least about 1 wt %" means "at least 1 wt % or about 1 wt %." Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed is:

1. A method of making polyglycerol comprising:
heating glycerol at a temperature of about 120° C. to about 160° C. at a pressure below about 400 mmHg in the absence of a glyceride and in the presence of a catalytic amount of an acid selected from the group consisting of sulfuric acid, triflic acid, hydrochloric acid, hexafluorophosphoric acid, and tetrafluoroboric acid, or mixtures thereof, and removing water during the heating step;
wherein the polyglycerol has an $\overline{M}_w$ of at least 50,000 g/mol.

2. The method of claim 1, wherein the acid is sulfuric acid.

3. The method of claim 1, wherein the glycerol is heated at a temperature of about 130° C. to about 150° C.

4. The method of claim 1, wherein the glycerol is heated at a temperature of about 140° C.

5. The method of claim 1, wherein the glycerol is heated at a pressure at or below about 200 mmHg.

6. The method of claim 1, wherein the catalytic amount of acid is about 1 wt % to about 5 wt %.

7. The method of claim 1, wherein the heating step is performed in the absence of an added epoxide.

8. The method of claim 1, wherein the glycerol is heated under an inert atmosphere.

9. The method of claim 1, wherein the polyglycerol is not gelled.

10. The method of claim 1, wherein less than about 75 mol % of the glycerol hydroxyl groups are converted.

11. The method of claim 1, wherein about 70 mol % to about 75 mol % of the glycerol hydroxyl groups are converted.

12. The method of claim 1, wherein the critical extent of reaction, $p_c$, is less than or equal to about 80 mol %.

13. The method of claim 1, wherein the critical extent of reaction, $p_c$, is about 70 mol % to about 80 mol %.

14. The method of claim 1, wherein the polyglycerol has an $\overline{M}_w$ from about 50,000 g/mol to about 120,000 g/mol.

15. The method of claim 1, wherein the polyglycerol has an $\overline{M}_n$ of at least 1,500 g/mol.

16. The method of claim 1, wherein the polyglycerol has an $\overline{M}_n$ from about 1,500 g/mol to about 4,000 g/mol.

17. The method of claim 1, further comprising:
    monitoring the amount of water produced during the heating step; and
    discontinuing heating prior to reaching the critical extent of the reaction.

18. The method of claim 1, further comprising monitoring the conversion of glycerol to polyglycerol.

19. The method of claim 1, further comprising purifying the polyglycerol.

20. The method of claim 1, further comprising:
    diluting the polyglycerol with water; and
    contacting the diluted polyglycerol with an ion exchange resin.

21. A method of making polyglycerol comprising:
    heating a mixture consisting essentially of glycerol and a catalytic amount of an acid selected from the group consisting of sulfuric acid, triflic acid, hydrochloric acid, hexafluorophosphoric acid, and tetrafluoroboric acid, or mixtures thereof, at a temperature of about 120° C. to about 160° C. and a pressure below about 400 mmHg, and removing water during the heating step;
    wherein the polyglycerol has an $\overline{M}_w$ of at least 50,000 g/mol.

22. The method of claim 21, wherein the acid is sulfuric acid.

* * * * *

UNITED STATES PATENT AND TRADEMARK OFFICE
CERTIFICATE OF CORRECTION

PATENT NO. : 8,704,005 B2
APPLICATION NO. : 13/979589
DATED : April 22, 2014
INVENTOR(S) : Dube et al.

It is certified that error appears in the above-identified patent and that said Letters Patent is hereby corrected as shown below:

Title Page, insert illustrative figure as shown below:

-- 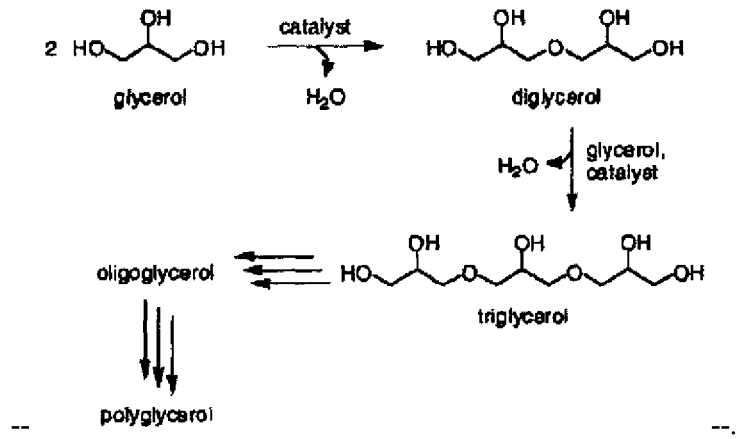 --.

References Cited

On Title Page 2, Item (56), under "OTHER PUBLICATIONS", in Column 1, Line 7, delete "Molecuar" and insert -- Molecular --, therefor.

On Title Page 2, Item (56), under "OTHER PUBLICATIONS", in Column 2, Line 16, delete "polyglycero-based" and insert -- polyglycerol-based --, therefor.

On Title Page 2, Item (56), under "OTHER PUBLICATIONS", in Column 2, Line 21, delete "Appin." and insert -- Appln. --, therefor.

In the Specification

In Column 2, Lines 34-35, delete "polyglycerol" and insert -- polyglycerol. --, therefor.

Signed and Sealed this
Twenty-first Day of April, 2015

Michelle K. Lee
*Director of the United States Patent and Trademark Office*

CERTIFICATE OF CORRECTION (continued)
U.S. Pat. No. 8,704,005 B2

In Column 2, Line 37, delete "$\mathbf{\overline{M}}_w$," and insert -- $\overline{M}_w$ --, therefor.

In Column 2, Line 38, delete "$\mathbf{\overline{M}}_w$," and insert -- $\overline{M}_w$ --, therefor.

In Column 8, Line 64, delete "where α" and insert -- where a --, therefor.

In Column 12, Line 15, delete "$\mathbf{\overline{M}}_w$," and insert -- $\overline{M}_w$ --, therefor.